United States Patent [19]

Tuomanen

[11] Patent Number: 4,661,345

[45] Date of Patent: Apr. 28, 1987

[54] METHOD FOR TREATING PERTUSSIS

[75] Inventor: Elaine Tuomanen, New York, N.Y.

[73] Assignee: The Rockefeller University, New York, N.Y.

[21] Appl. No.: 705,739

[22] Filed: Feb. 26, 1985

[51] Int. Cl.[4] .................. A61K 31/70; A61K 39/395; A61K 37/04

[52] U.S. Cl. .......................................... 424/85; 514/8; 514/23; 514/62; 514/54; 436/547; 530/397

[58] Field of Search ................ 424/85, 87; 260/112 B; 514/62, 23, 8, 54; 436/547

[56] References Cited

PUBLICATIONS

Tuomanen et al, "Characterization of Antibody Inhibiting . . . Cells", *J. Clinical Microbiol.* vol. 20(2) 1984, pp. 167–170.

Sato et al, "Affinity of Pertussis Toxin Produced by Bordetella-Pertussis . . . Toxin", *J. Microbial Methods* 1(2) 1983, pp. 99–110 (abstract).

Sato et al, "Monoclonal Antibody Against Pertussin Toxin:" *Infect and Immunity* 46(2) 1984, pp. 422–428.

Tuomanen et al, "Adherence of *B. pertussis* to . . . Cells," *J. of Infect. Disease,* vol. 148(1) 1983, pp. 125–130.

Irons et al, "Isolation of the LP Factor . . . Affinity Chromatography"; *Biochim Biophys Acta* 580, 1979, pp. 175–185.

Iwata et al, "Modulation of the Biological Activities of IgE-Binding Factor", *J. Immunol,* vol. 130(4) 1983, pp. 1802–1808.

*Primary Examiner*—John Kight
*Assistant Examiner*—Garnette D. Draper
*Attorney, Agent, or Firm*—Wyatt, Gerber, Shoup, Scobey and Badie

[57] ABSTRACT

Method of inhibiting the adhesion of *Bordetella pertussis* to the cilia of human respiratory cells to treat pertussis, agents and compositions useful in the method. Agents are also useful to stimulate the production of antibodies.

24 Claims, No Drawings

METHOD FOR TREATING PERTUSSIS

BACKGROUND OF THE INVENTION

Whooping cough, or pertussis, is a non-invasive respiratory infection established by the adherence of the bacteria *Bordetella pertussis* (Bp) to the cilia of human respiratory cells. The disease is virtually 100% contagious and sometimes fatal. It is world wide, serious and often epidemic. An epidemic in Japan in 1979 resulted in 41 deaths from a total of 13,105 cases.

The incidence of pertussis in a highly vaccinated population as in the United States is estimated at about 300 per 100,000. In less developed countries where vaccination is not the norm infant mortality due to pertussis is close to this same figure. The World Health Organization currently recommends that every child, worldwide, receive protection from whooping cough.

The current whole cell vacine available in the United States and Europe is 70% to 90% effective, but has an unacceptably high rate of toxicity including death, particularly amongst infants who are the prime targets of the disease. Moreover, both children and adults who have been protected by vaccination may be infected without clinical manifestations. This population colonized with the bacteria is a source of infections to others.

An additional problem with control of pertussis is that it is difficult to identify until after the disease has become established in the patient. Thus the physician's role is often reduced to attempts to attenuate the clinical manifestations of pertussis, to prevent secondary infections, and to treat superinfections with other pathogenic organism, for example *Haemophilus influenzae,* group A streptococci and pneumonococci. Such superinfections are not uncommon, have grave prognoses and often result in death.

A system which could be useful in the control and possible eradication of pertussis, which would protect infants without exposure to potentially toxic vaccines and at the same time protect adults and eliminate both children and adults as sources of infection would be:

1. Defer use of vaccines by conferring passive protection on infants until they are at least six months of age to permit the infant's immune system to mature and avoid the possibility of serious adverse reactions associated with early vaccination.
2. Use of vaccines which would be safe and effective with older infants and adults.
3. Use of vaccines with pregnant women and possible transfer of immunity to infants in utero and through the colostrum.

The problem with this proposed regimen is that heretofore there has been no practical method for conferring passive protection on infants pending vaccination. An agent capable of generating passive protection would also be useful to protect individuals at risk because of exposure to Bp. This could include newborns, children in school, hospital personnel, unvaccinated children and adults, and immunocompromised children. The value of such a prophylactic agent would be enhanced if it could also be used to treat an existing infection.

As indicated above, Bp infects humans by adherence to the cilia of the epithelial cells of the respiratory tract. The infection establishes itself when the organism multiplies and spreads along the same cilia or to adjacent cilia. An agent to prevent the original infection and/or expansion from the original infection site would be of great therapeutic value. Such agents have now been found.

THE INVENTION

It has now been discovered that it is possible to inhibit adherence of Bp to the cilia of human respiratory cells by bronchial administration of a chemical compound which is characterized by the presence in its molecule of a galactosido-glucose unit or a derivative of such unit. By the use of the method of this invention it is possible to treat humans at risk of pertussis, i.e. to treat prophylactically, or to treat an overt infection, i.e. therapeutically. The word "treat" and variations thereof as used herein is intended to cover both prophylactic and therapeutic use of the agents of the invention.

The agents of the invention may be relatively simple molecules such as lactose, or they can be complex carbohydrates including glycolipids and glycoproteins. They can also be mixtures of these products so long as one component of the mixture contains the common unifying feature of all of the agents of the invention. This feature is the presence of an available galactosido-glucose unit.

The least complex carbohydrate having the requisite structure is lactose or milk sugar. This disaccharide is better defined by the chemical name 1, 4-(β-D-galactosido)-D-glucose which precisely defines the linkage between the galactose and the glucose monomer as well as the configuration of the hydroxyl groups and hydrogen atoms on the various carbon atoms.

It presently appears that the exact linkage between the galactose and the glucose does not affect the utility of the agents of the invention. In lactose the linkage is 1, 4 but there may be other linkages, for example 1, 3 without significant loss of therapeutic activity. Therefore, for convenience the basic unit of this invention is referred to as a galactosido-glucose unit without reference to the position of the linkage, whether the number one carbon atom is alpha or beta or whether the stereoisomeric form is L or D. Analogs and derivatives of such units also manifest adhesion inhibiting properties.

One example of simple derivatives of the galactosido-glucose unit which is useful in the practice of the invention is galactosido-N-acylglucosamine wherein the acyl group contains up to six carbon atoms. The preferred embodiment of this class is galactosido-N-acetylglucosamine. As indicated above, the linkage between the carbohydrate monomers may be 1, 4 or another linkage.

Bp adherence to cilia is associated with bacterial proteins on the surface of the microorganism which recognize and bind to carbohydrates on the cilia of the host cells. For convenience these bacterial proteins are termed adhesins and the host cell carbohydrates are termed receptors. It has been discovered that it is possible to inhibit adhesion and thereby treat the infection by administering to an infected individual or an individual at risk of infection an effective amount of a chemical compound of defined structure to occupy those sites on the adhesins which recognize and bind to the receptors, thereby to neutralize the ability of the adhesion to bind to the receptor. The selected compounds effectively mimic the receptors and deny the receptors to the bacteria. This makes it possible for the bacteria to be cleared from the respiratory passages by the ciliary escalator or another of the bodies natural defense mechanisms.

Chemical compounds which will mimic the receptors, block the adhesins and prevent joining of the bacteria to the cilia have a common sugar sequence in which the monomer carbohydrates galactose and glucose are joined together to form a dimer unit which may be the simple molecule lactose or some more complex structure of which the dimer unit is a minor or major component. Examples of complex carbohydrates which are useful in this invention are lactoferrin, fetuin, fibronectin, heptaglobin and pneumonococcal polysaccharides such as pneumovac which is available from Merck. These products are all high molecular weight compounds or mixtures of compounds, and are all known. For convenience herein they are termed complex carbohydrates although they may have other moieties in their structure.

The effectiveness of the dimer unit derives from its resemblance to the host receptor. This is supported by the fact that lectins which are known to bind to molecules carrying a galactosido glucose unit can block adherence of Bp to the cilia of human respiratory cells when allowed to bind to such cells prior to the addition of bacteria.

A complete understanding of this invention requires an understanding of the assay procedure used to determine the extent of the binding of Bp to human ciliated respiratory cells. It is described in detail by Tuomanen and Hendley in the Journal of Infectious Diseases 148: 125 (1983) which is incorporated herein by reference.

In the procedure, Bp organisms suspended in 199S (the known medium 199 [M.A. Bioproducts, Walkersville, MD.] supplemented with 0.3% bovine serum albumin, 25 mM HEPES [Calbiochem, Los Angeles], 10 mM L-glutamine and 0.15% $NaHCO_3$) are passed three times through a 21-gauge needle to produce a suspension of single organisms, incubated at 37°C. for 30 minutes and then passed through the needle again. The concentration of organisms is estimated using a Petroff-Hauser counting chamber (Hauser Scientific, Blue Bell, Pa.). A bacterial suspension (0.5 ml) is combined with 0.5 ml of 199S containing $0.5\text{–}1\times10^5$ of human ciliated cells. The bacteria-cell mixture is incubated for 3 hours at 37° C. on a shaker at 120 rpm. Cells are rinsed free of nonadherent bacteria over a polycarbonate membrane filter (pore size, 3Nm; Nuclepore, Pleasonton, Calif.) with 50 ml of 199S/VCB. 199S/VCB contains one part 199S and three parts viral collecting broth (beef-heart infusion broth with 1% bovine syrum albumin). Cells are eluted from the filter into 199S/VCB, sedimented at 250 g for 15 minutes, resuspended in 0.1 ml PBS and spread onto a slide. Air dried cells are fixed in acetone for 10 minutes.

Bp organisns that are adherent to ciliated cells are stained with fluorescent antibody specific for Bp (Difco) and 1% Evan's blue counterstain. Stained slides are coded and read in a blinded fashion using a microscope equipped with phase-contact illumination and an epifluorescence unit. After location of a ciliated cell under phase, illumination of the field is changed to fluorescence, and organisms that are enmeshed in the cilia are counted. The mean number of adherent bacteria is calculated by examining 25 ciliated cells per slide.

Bp incubated with human respiratory epithelial cells are observed to adhere exclusively to the tufts of cilia. Incubation of $2\times10^9$ Bp with $10^5$ ciliated cells results in adherence of a mean of approximately 5 organisms per ciliated cell.

A modification of this assay was used to demonstrate the inhibitory activity of compounds useful for this invention. In these assays, chemical compounds of the type defined were incubated with Bp for 3 minutes at 37° C. and the mixture was added to human ciliated cells for the standard three hour assay procedure described above. Inhibition was considered to have taken place when there was a decrease in the number of adherent bacteria per cell.

The results with some of the tested materials are shown in the following Table 1. A negative sign indicates no reduction in adherence. A positive sign indicates a reduction to less than one adherent bacteria per cell. A double positive sign indicates no observable adherence.

TABLE 1

| | |
|---|---|
| Complex Carbohydrates | |
| Lactoferrin | ++ |
| Fetuin | + |
| Fibronectin | + |
| Human chorionic gonadotropin | − |
| IgA | − |
| Pneumovac | + |
| Haptoglobin | + |
| Breast milk oligosaccharides | + |
| Breast milk oligosaccharides without lactose | − |
| Simple Carbohydrates | |
| D-Fucose | − |
| L-Fucose | − |
| Lactose | ++ |
| D-Galactose | − |
| Mannose | − |
| N—acetyl glucosamine | − |

All of the above complex carbohydrates are pure compounds or mixtures. Those that are inhibitory have the common characteristic that they contain either in a single compound or in a compound of the mixture a galactosido-glucose carbohydrate dimer unit. Those that are not inhibitory, although they do contain carbohydrate units or segments do not contain a galactosido-glucose unit.

Of the simple carbohydrates listed, only lactose has the requisite structure, and only lactose is inhibitory.

The fact that lactose free breast milk oligosaccharides are not inhibitory is indicative of the importance of the presence of the galactosido-glucose dimer.

A further indication of the importance of the galactosido-glucose segment in the active compounds is the behavior of lectins in the assay. Lectins are plant proteins with a high affinity for specific sugar residues. They are widely employed as probes to locate and identify specific carbohydrate groups on membranes of eucaryotic cells. Several are known that are specifically reactive with galactosido- glucose segments. If such segments were present as receptors on the cilia of human respiratory cells, these specific lectins would adhere to them thereby denying these receptors to the adhesins of Bp.

For this particular study, human respiratory cells were allowed to bind to lectins of known specificity before these same cells were used in the assay described above.

Table 2 lists those lectins which were inhibitory and those which were not inhibitory using the same criteria defined above.

TABLE 2

| Lectins | |
| --- | --- |
| Lotus tetragonolobus | ++ |
| Arachis hypogaea | + |
| Concanavalin A | − |
| Triticum Vulgaris | − |
| Bandeiraea simplicifolia | − |
| Ulex europeus | − |
| Ptilota plumosa | − |

Those lectins which are positive are known as probes for galactosido-glucose segments. Those that are negative are not probes for this unit.

It is clear from these results that chemical compounds with the selected segment function by blocking the carbohydrate seeking adhesins and neutralizing their ability to anchor the Bp bacteria to the receptors on the cilia of human respiratory cells. These compounds, bronchially administered to humans in need of treatment will benefit the individual in need of such treatment by inhibiting the adherence of Bp bacteria to the epithelial respiratory cells. Lectins cannot be so employed because they are toxic.

The therapeutic compositions of this invention are compositions for bronchial administration and comprise the selected chemical compound in a physiologically acceptable carrier suitable for such administration. Typically useful carriers include water, isotonic sodium chloride, physiologically acceptable buffers and the like. Preservatives such as benzyl alcohol may be included. In certain instances, particularly if the composition is used to treat an established infection, it may be helpful to incorporate therapeutic quantities of an antibotic such as erythromycin in the composition to assist in combatting superinfections.

The concentration of the chemical compound with the carbohydrate segment in the useful compositions of this invention may vary over a wide range depending on a number of factors. For example, compositions for infant use will be less concentrated than those for adult use, since an effective amount for an infant will normally be less than for an adult. The concentration may vary depending on whether the total dosage is to be administered in one treatment or in a series of succesive treatments extending over one or more days. Additionally, an effective concentration will vary with the molecular weight of the selected compound. High molecular weight materials where the dimer unit is only a small segment of the structure will require higher concentrations then their lower molecular weight conterparts. This generalization might be modified if the high molecular weight compound contains several adhesin blocking segments per molecule.

Typically useful compositions may contain from about 0.1% to 1% by weight based on the total weight of the compound with the dimer segment disposed in a pharmaceutically acceptable carrier.

In dosage unit forms the compositions will be provided in nebulizers from which they can be administered as a spray. For convenience each nebulizer may contain several dosage units to permit multiple administrations. Many forms of nebulizers are in common use including, for example those in which the composition is packed under the pressure of an inert gas such as carbon dioxide or nitrogen. The container may be fitted with a metering valve so that predetermined quantities of the compositions can be delivered. Typically useful dosage unit forms of this invention may contain from 1 Ng to 100 mg chemical compound per dosage unit. For bronchial administration a dosage unit may be from about 0.02 to 0.1 ml.

Those skilled in the art will recognize that the galactosido-glucose unit must be in a position to react with the adhesin in order for the chemical compound carrying it to be a useful agent for the practice of this invention. Many complex, high molecular weight substances such as glycoproteins or glycolipids may carry one or more galactosido-glucose segments, but these may be sterically hindered so that they are not spatially available for, reaction. It will be understood therefore that when reference is made to agents of the invention, the intent is to include only those compounds in which the carbohydrate dimer is available to react with the adhesins.

Some of the active compounds useful in this invention are of sufficiently high molecular weight to be immunogenic. Such compounds when administered in accordance with the practice of the invention will stimulate the production of antibodies including antibodies to the carbohydrate dimer. As is clear, particularly from the above discussion of lectins, the carbohydrate dimer is a component of the cilia of human respiratory cells. Therefore antibodies which are stimulated to production by the administration of a compound containing the dimer will bind to the dimer of the cilia and produce immunity to Bp. When the compositions of this invention are used to stimulate antibodies, they are not limited to bronchial administration. They may also be given orally or parenterally.

The antibody can be isolated if desired. One useful method is to pass the serum containing it over a chromatographic column to which the antigen which stimulated the antibody has been adsorbed. The antibody will preferentially react with the antigen. The resulting conjugate can be collected from the column and separated into its constitutent parts. The antibody is useful for conferring passive protection by preferential binding to cilia receptors.

Chemical compounds useful in this invention which are not themselves immunogenic can be converted to antibody stimulating products by combining them with a carrier of sufficiently high molecular weight so that the compound functions as an antigenic hapten. Albumin is a carrier often used with such haptens. It is useful to convert the non-antigenic compounds of this invention into immunogenic haptens.

What is claimed is:

1. A method of inhibiting adherence of *Bordetella pertussis* to the cilia of respiratory epithelial cells of humans which comprises bronchial administration of a therapeutic composition containing in an amount which is effective to inhibit such adherence a chemical compound characterized by the presence in its molecule of a galactosido-glucose unit which is available to react with adhesins on the cilia of human respiratory epithelial cells to which Bordetella pertussis normally adheres.

2. A method as in claim 1 wherein the chemical compound is lactose.

3. A method as in claim 1 wherein the chemical compound is a galactosido-N-acylglucosamine wherein the acyl group contains up to six carbon atoms.

4. A method as in claim 3 wherein the acyl group is the acetyl group.

5. A method as in claim 1 wherein the chemical compound is a complex carbohydrate selected from the group consisting of lactoferrin, fetuin, fibronectin and haptoglobin.

6. A therapeutic composition in dosage unit form for bronchial administration to a human to inhibit adherence of *Bordetella pertussis* to the cilia of respiratory epithelial cells comprising a physiologically acceptable carrier and, as the principal active ingredient from 1 Ng to 100 mg of a chemical compound which will inhibit adherence of *Bordetella pertussis* to the cilia or respiratory epithelial cells of humans, said chemical compound characterized by the presence in the molecule of a galactosido-glucose unit which is available to react with adhesins on the cilia of human respiratory epithelial cells to which *Bordetella pertussis* normally adheres.

7. A composition as in claim 6 wherein the chemical compound is lactose.

8. A composition as in claim 6 wherein the chemical compound is a galactosido-N-acylglucosamine wherein the acyl group contains up to six carbon atoms.

9. A composition as in claim 8 wherein the acyl group is the acetyl group.

10. A composition as in claim 6 wherein the chemical compound is a complex carbohydrate selected from the group consisting of lactoferrin, fetuin, fibronectin and haptoglobin.

11. A therapeutic composition for bronchial administration comprising a physiologically acceptable carrier and, as the principal active ingredient from 0.1% human to inhibit adherence of *Bordetella pertussis* to the cilia of respiratory epithelial cells to 1% by weight based on the total weight of a chemical compound which will inhibit adherence of *Bordetella pertussis* to the cilia or respiratory epithelial cells of humans, said chemical compound characterized by the presence in the molecule of a galactosido-glucose unit which is available to react with adhesions on the cilia of human respiratory epithelial cells to which *Bordetella pertussis* normally adheres.

12. A composition as in claim 11 wherein the chemical compound is lactose.

13. A composition as in claim 11 wherein the chemical compound is a galactosido-N-acylglucosamine wherein the acyl group contains up to six carbon atoms.

14. A composition as in claim 13 wherein the acyl group is the acetyl group.

15. A composition as in claim 11 wherein the chemical compound is a complex carbohydrate selected from the group consisting of lactoferrin, fetuin, fibronectin and haptoglobin.

16. A method of stimulating the production of an antibody which will adhere to the cilia of respiratory epithelial cells of humans thereby inhibiting adherence of *Bordetella pertussis* to said cells which comprises administration to a human of a physiologically acceptable composition containing an immunogenically stimulating amount of a chemical compound characterized by the presence of a galactosido-glucose unit which is available to react with adhesions on cilia of human respiratory epithelial cells to which *Bordetella pertussis* normally adheres.

17. A method as in claim 16 wherein the unit is lactose.

18. A method as in claim 16 wherein the unit is a galactosido-N-acylglucosamine wherein the acyl group contains up to six carbon atoms.

19. A method as in claim 18 wherein the acyl group is the acetyl group.

20. A method as in claim 16 wherein the chemical compound is selected from the group consisting of lactoferin, fetuin, fibronectin and haptoglobin.

21. An antibody produced by the method of claim 16.
22. An antibody produced by the method of claim 17.
23. An antibody produced by the method of claim 18.
24. An antibody produced by the method of claim 19.

* * * * *